United States Patent
Yao et al.

(10) Patent No.: US 11,013,414 B2
(45) Date of Patent: May 25, 2021

(54) MULTISPECTRAL SYNCHRONIZED IMAGING

(71) Applicant: SYNAPTIVE MEDICAL INC., Toronto (CA)

(72) Inventors: Ze Shan Yao, Toronto (CA); Piotr Kuchnio, Toronto (CA); Michael Frank Gunter Wood, Toronto (CA); Tammy Kee-Wai Lee, Toronto (CA); Yanhui Bai, Toronto (CA); Michael Peter Bulk, Toronto (CA); Christopher Thomas Jamieson, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 0 days.

(21) Appl. No.: 15/504,057

(22) PCT Filed: May 10, 2016

(86) PCT No.: PCT/IB2016/052678
§ 371 (c)(1),
(2) Date: Feb. 15, 2017

(87) PCT Pub. No.: WO2017/194993
PCT Pub. Date: Nov. 16, 2017

(65) Prior Publication Data
US 2018/0153408 A1  Jun. 7, 2018

(51) Int. Cl.
A61B 5/00 (2006.01)
A61B 34/20 (2016.01)
(Continued)

(52) U.S. Cl.
CPC .......... *A61B 5/0075* (2013.01); *A61B 5/0042* (2013.01); *A61B 5/0071* (2013.01);
(Continued)

(58) Field of Classification Search
CPC ............... A61B 5/0075; A61B 5/0071; A61B 2562/0233; A61B 1/00186; A61B 1/0684; A61B 1/063; A61B 1/0638
See application file for complete search history.

(56) References Cited

U.S. PATENT DOCUMENTS 5,074,306 A * 12/1991 Green ................. A61B 5/0071
600/317
5,400,791 A * 3/1995 Schlier ................ A61B 3/1241
600/317
(Continued)

FOREIGN PATENT DOCUMENTS

WO  2006040773 A1  4/2006
WO  2012/048890 A1  4/2012

OTHER PUBLICATIONS

Liu et al., "In vivo targeting of colonic dysplasia on fluorescence endoscopy with near-infrared octapeptide" Gut, vol. 62, issue 3, pp. 395-403, Mar. 2013, author manuscript available Mar. 2014 (Year: 2014).*

(Continued)

*Primary Examiner* — Katherine L Fernandez
*Assistant Examiner* — Colin T. Sakamoto

(57) ABSTRACT

A multispectral synchronized imaging system is provided. A multispectral light source of the system includes: blue, green and red LEDs, and one or more non-visible light sources, each being independently addressable and configured to emit, in a sequence: at least visible white light, and non-visible light in one or more given non-visible frequency ranges. The system further includes a camera and an optical filter arranged to filter light received at the camera, by: transmitting visible light from the LEDs; filter out non-visible light from the non-visible light sources; and otherwise transmit excited light emitted by a tissue sample excited by non-visible light. Images acquired by the camera (Continued)

are output to a display device. A control unit synchronizes acquisition of respective images at the camera for each of blue light, green light, visible white light, and excited light received at the camera, as reflected by the tissue sample.

20 Claims, 12 Drawing Sheets

(51) Int. Cl.

| | | |
|---|---|---|
| *A61B 5/026* | (2006.01) | |
| *G01J 3/443* | (2006.01) | |
| *A61B 90/00* | (2016.01) | |
| *A61B 5/06* | (2006.01) | |
| *G01J 3/28* | (2006.01) | |
| *G01J 3/10* | (2006.01) | |
| *G01J 3/02* | (2006.01) | |
| *A61B 90/20* | (2016.01) | |
| *A61B 90/30* | (2016.01) | |
| *A61B 17/34* | (2006.01) | |

(52) U.S. Cl.
CPC .......... *A61B 5/0077* (2013.01); *A61B 5/0082* (2013.01); *A61B 5/0084* (2013.01); *A61B 5/026* (2013.01); *A61B 5/061* (2013.01); *A61B 5/748* (2013.01); *A61B 5/7425* (2013.01); *A61B 34/20* (2016.02); *A61B 90/361* (2016.02); *G01J 3/0248* (2013.01); *G01J 3/10* (2013.01); *G01J 3/2803* (2013.01); *G01J 3/2823* (2013.01); *G01J 3/443* (2013.01); *A61B 5/0261* (2013.01); *A61B 5/725* (2013.01); *A61B 17/34* (2013.01); *A61B 90/20* (2016.02); *A61B 2034/2055* (2016.02); *A61B 2090/309* (2016.02); *A61B 2562/0233* (2013.01); *A61B 2562/0242* (2013.01); *G01J 2003/106* (2013.01); *G01J 2003/2826* (2013.01)

(56) References Cited

U.S. PATENT DOCUMENTS

| | | | | |
|---|---|---|---|---|
| 5,603,328 | A | * | 2/1997 | Zucker .................. A61B 5/015 250/330 |
| 5,910,816 | A | * | 6/1999 | Fontenot .............. A61B 5/0059 348/162 |
| 6,373,568 | B1 | * | 4/2002 | Miller ...................... G01J 1/08 356/326 |
| 2006/0106282 | A1 | * | 5/2006 | Bala ..................... A61B 1/0638 600/108 |
| 2006/0241495 | A1 | | 10/2006 | Kurtz |
| 2010/0194860 | A1 | * | 8/2010 | Mentz ................. H04M 1/0264 348/47 |
| 2012/0130258 | A1 | * | 5/2012 | Taylor ...................... A61B 3/13 600/476 |
| 2015/0099979 | A1 | | 4/2015 | Caves et al. |
| 2017/0215711 | A1 | * | 8/2017 | Kobayashi ......... A61B 1/00186 |

OTHER PUBLICATIONS

Chen et al., "Single camera imaging system for color and near-infrared fluorescence image guided surgery" Biomedical Optics Express Aug. 2014 (Year: 2014).*
Boas et al., "Laser speckle contrast imaging in biomedical optics" J. of Biomedical Optics, 15(1), 011109 (2010) (Year: 2010).*
Castaneda, Humberto, International Search Report, PCT Application No. PCT/IB2016/052678, dated Dec. 21, 2016.
Everdell, N.L. et al., "Multispectral imaging of the ocular fundus using light emitting diode illumination", Review of Scientific Instruments, 81, 093706 (2010), pp. 093706-1 to 093706-9.
Written Opinion of the International Searching Authority dated Dec. 19, 2016 for PCT International Patent Application No. PCT/IB2016/052678.
Leica Microsystems (Schweiz) AG, Leica FL800, Leica Microsystems, 2011.
Novadaq, Pinpoint Endoscopic Fluorescence Imaging, NOVADAQ, 2016, http://novadaq.com/products/pinpoint-endoscopic-fluorescence-imaging.

* cited by examiner

MULTISPECTRAL SYNCHRONIZED IMAGING

CROSS-REFERENCE TO RELATED APPLICATION(S)

This document is a national phase entry application which claims the benefit of, and priority to, International Patent Application No. PCT/IB2016/052678, filed on May 10, 2016, entitled "MULTISPECTRAL SYNCHRONIZED IMAGING," which herein is incorporated by reference in its entirety.

FIELD

The specification relates generally to medical imaging and methods for minimally invasive therapy and image guided medical procedures, and specifically to a system and method of multispectral synchronized imaging.

BACKGROUND

Image guided medical procedures can include fluorescence guided surgery (FGS), which is a medical imaging technique used to facilitate the delineation of the tumor margin during surgery or vascular angiography. With the current mainstream technology, changing from normal white light surgery (WLS) to FGS requires a mechanical filter wheel for switching of the emission filter on the camera side and another filter wheel on the illumination side to constrict the wavelength to an optimal narrow band. This mechanical switching creates a significant delay that restricts the possibility of concurrent imaging of WLS and FGS. In addition, Indocyanne green (ICG) fluorescent dye, used in FGS, has an emission spectrum (820 nm-860 nm) can overlap with infrared tracking pulses used in intermittent tracking of surgical tools, which can creates an artifact on the acquired image, restricting a concurrent tracking mode and ICG-FGS during surgery.

SUMMARY

The present disclosure is generally directed to image guided medical procedures using an access port. This port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Hence, an aspect of the present specification provides a multispectral synchronized imaging system comprising: a multispectral light source comprising: a light emitting diode (LED) array comprising: at least one blue LED, at least one green LED and at least one red LED; and one or more non-visible light sources arranged side by side with the LED array, each of the at least one blue LED, the at least one green LED, the at least one red LED, and the one or more non-visible light sources being independently addressable such that the multispectral light source is configured to emit in a sequence: at least visible white light, and non-visible light in one or more given non-visible frequency ranges; a camera arranged to receive light from a tissue sample illuminated by the multispectral light source in the sequence; an optical filter arranged to filter the light from the tissue sample received at the camera, the optical filter configured to: transmit visible light from the LED array; filter out non-visible light from the one or more non-visible light sources in the one or more given non-visible frequency ranges; and otherwise transmit excited light emitted by the tissue sample under excitation by the non-visible light from the one or more non-visible light sources; a display device; and, at least one control unit configured to: control the multispectral light source to emit the sequence; synchronize acquisition of respective images at the camera for each of blue light, green light, the visible white light, and the excited light received at the camera, as reflected by the tissue sample; and, output the respective images in a respective sequence to the display device.

The one or more non-visible light sources can comprise an ultraviolet (UV) LED, and the optical filter can be configured to filter out UV light from the UV LED, and transmit the excited light emitted by the tissue sample under excitation from the UV LED.

The one or more non-visible light sources can comprise an ultraviolet (UV) light source and an infrared (IR) light source, and the optical filter can be configured to: transmits light in a fluorescent range of about 430 nm to about 700 nm, and from about 820 nm to about 860 nm to allow light from emission of one or more of PpIX and ICG at the tissue sample to be imaged by the camera; and block light from both the UV light source and the IR light source from entering the camera The one or more non-visible light sources can comprise an infrared (IR) laser, and the optical filter can be configured to filter out IR light from the IR laser, and transmit the excited light emitted by the tissue sample under excitation from the IR laser.

The one or more non-visible light sources can comprise an infrared (IR) laser, and the system can further comprise a second optical filter, exchangeable for the optical filter under control by the at least one control unit; the second optical filter can be configured to transmit light from the IR laser. The IR laser can be operable in one of a diffused mode, when the optical filter is filtering light to the camera, and a speckled mode when the second optical filter is filtering light to the camera. The IR laser can be operable in a speckled mode when the second optical filter is filtering light to the camera, and the sequence can include green light emitted from the green LED, and blue light emitted from the blue LED, when the optical filter is filtering light to the camera, speckled laser light from the IR laser in the speckled mode, the green light and the blue light used for functional imaging of blood flow in the tissue sample.

The sequence can comprise the visible white light, and the non-visible light alternating.

The sequence can comprise the visible white light, green light, blue light, and the non-visible light alternating.

The sequence can comprise: one or more of a user-configured sequence; and simultaneous emission of light from two or more of the at least one blue LED, the at least one green LED, the at least one red LED.

Respective relative intensity of each of the at least one blue LED, the at least one green LED, the at least one red LED can be adjusted to change one or more of: color temperature of the visible white light; and color rendering of the respective images at the display device.

The multispectral synchronized imaging system can further comprise: a second camera arranged relative to the camera to acquire three-dimensional images of the tissue sample: and a second optical filter can be configured to:

transmit visible light from the LED array and transmit non-visible light from the one or more non-visible light sources in the one or more given non-visible frequency ranges. The one or more non-visible light sources can comprise an IR laser operable in one of a diffused mode and a speckled mode. The camera and the second camera can be configured to capture images independent of one another. Image capture times of each the camera and the second camera can be off-set with respect to one another.

The at least one control unit can be further configured to output the respective images in the respective sequence to the display device at a rate where the respective images appear simultaneously rendered to a human vision system.

The camera can comprise an optical camera.

The multispectral synchronized imaging system can further comprise a thermal camera arranged to receive the light from the tissue sample illuminated by the multispectral light source in the sequence.

The at least one control unit can comprise one or more ports configured for communicate with one or more of: external computing devices; electronic surgical devices; trackers; and infrared trackers.

The camera and the optical filter can be configured for use with a surgical port configured for corridor based surgery.

BRIEF DESCRIPTIONS OF THE DRAWINGS

For a better understanding of the various implementations described herein and to show more clearly how they may be carried into effect, reference will now be made, by way of example only, to the accompanying drawings in which.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Figure 1:
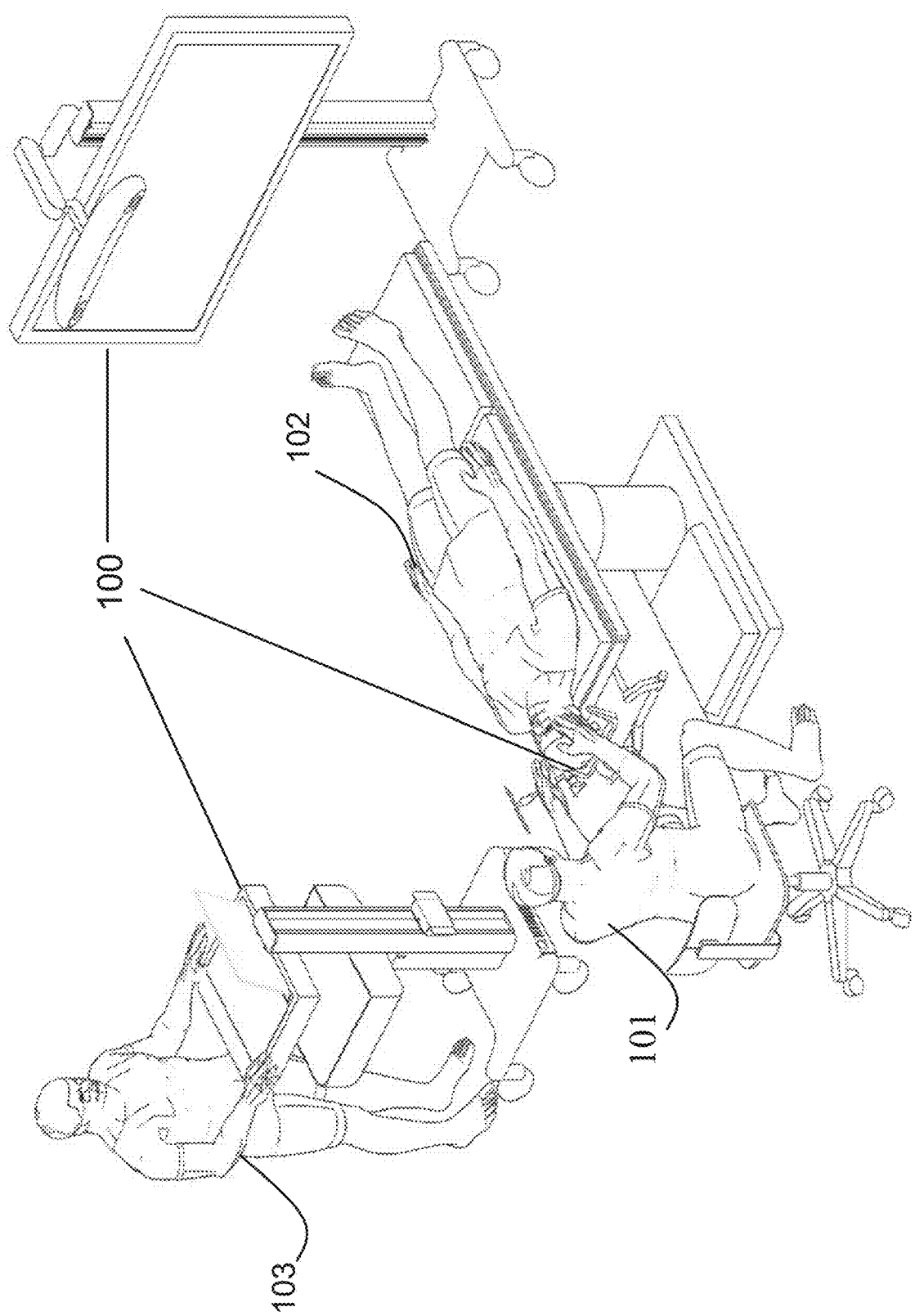
FIG. 1 shows an example operating room setup for a minimally invasive access port-based medical procedure, according to non-limiting implementations.

Referring to FIG. 1, a non-limiting example navigation system 100 is shown to support minimally invasive access port-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
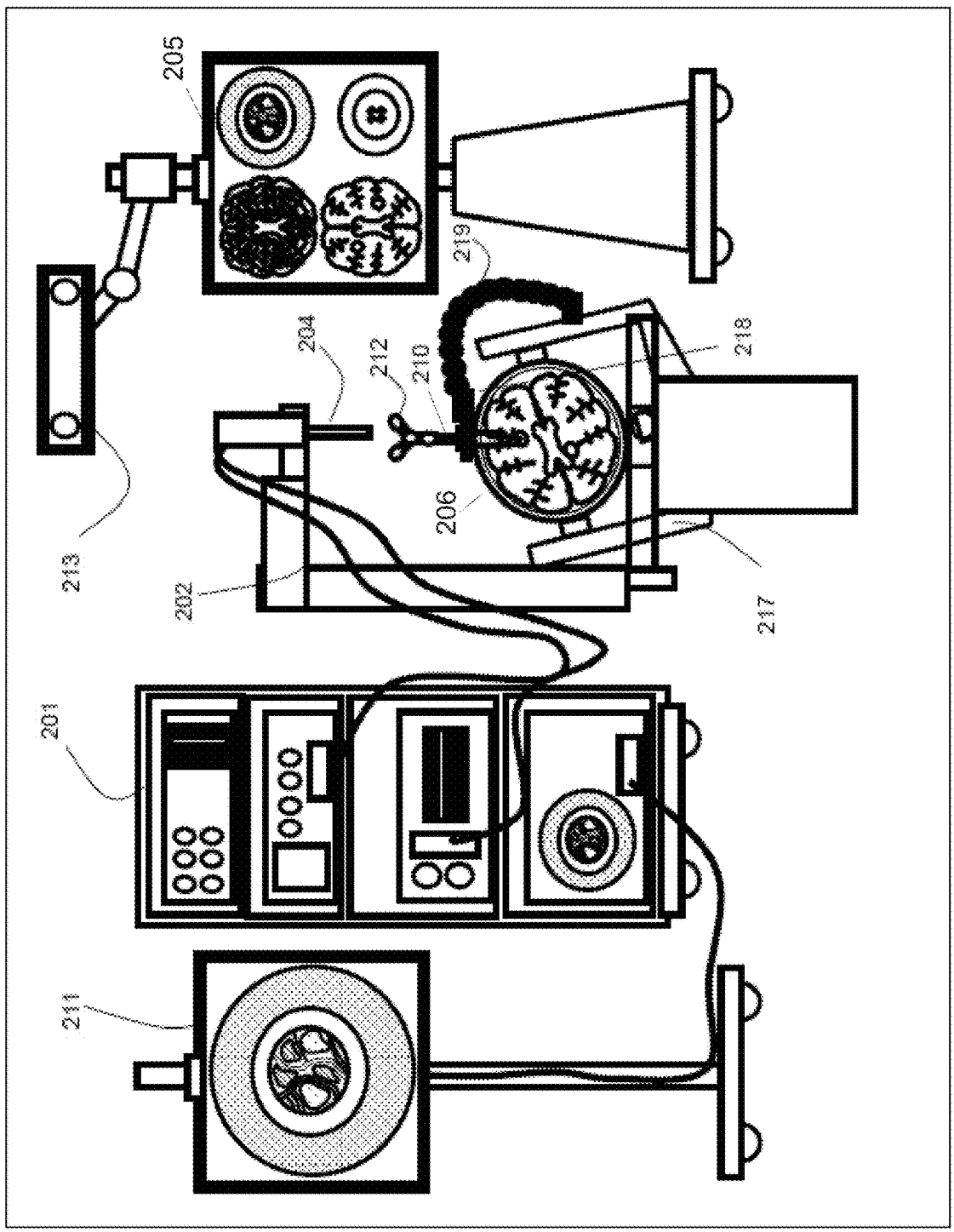
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
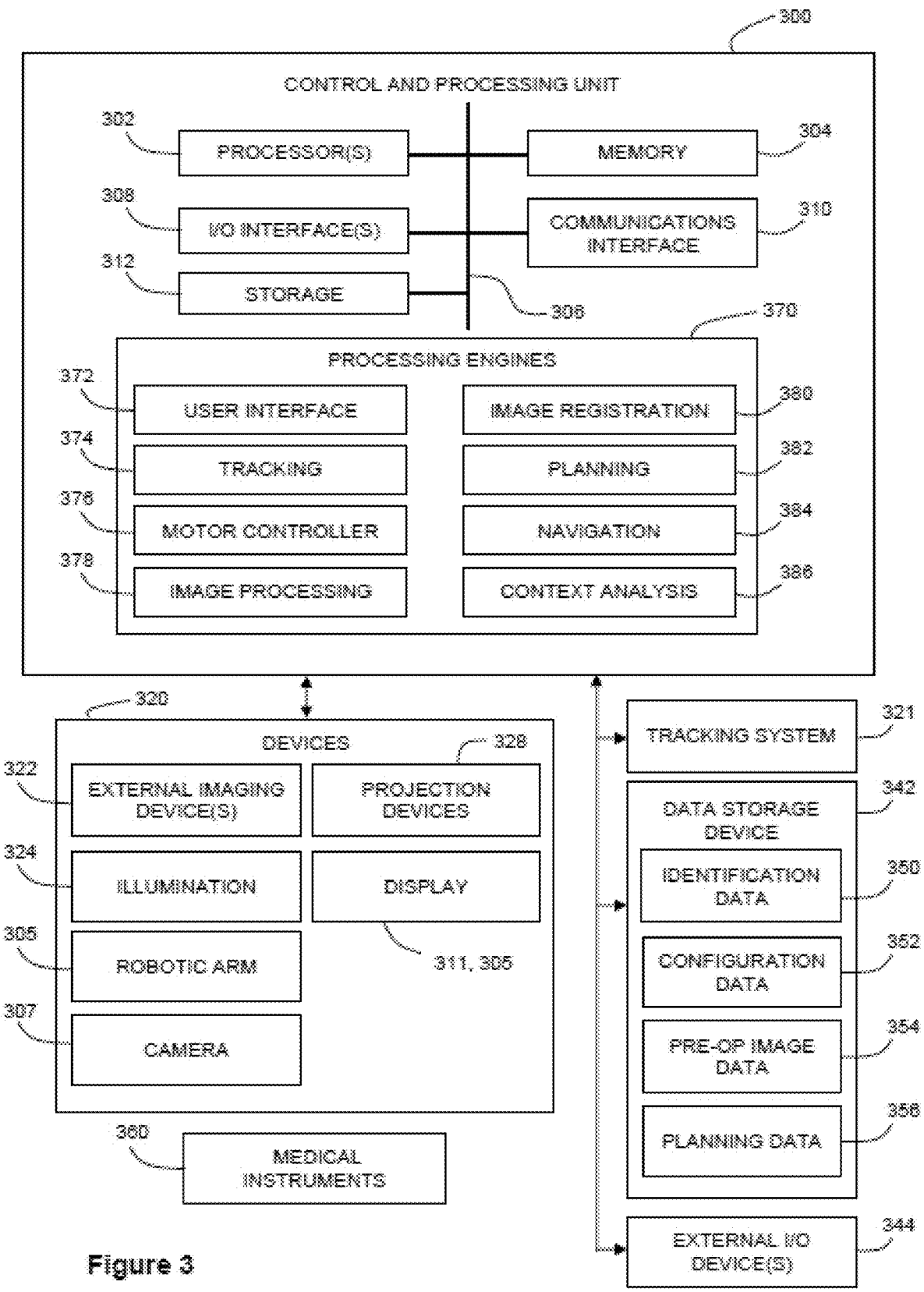
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, non-volatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like.

The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumors and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
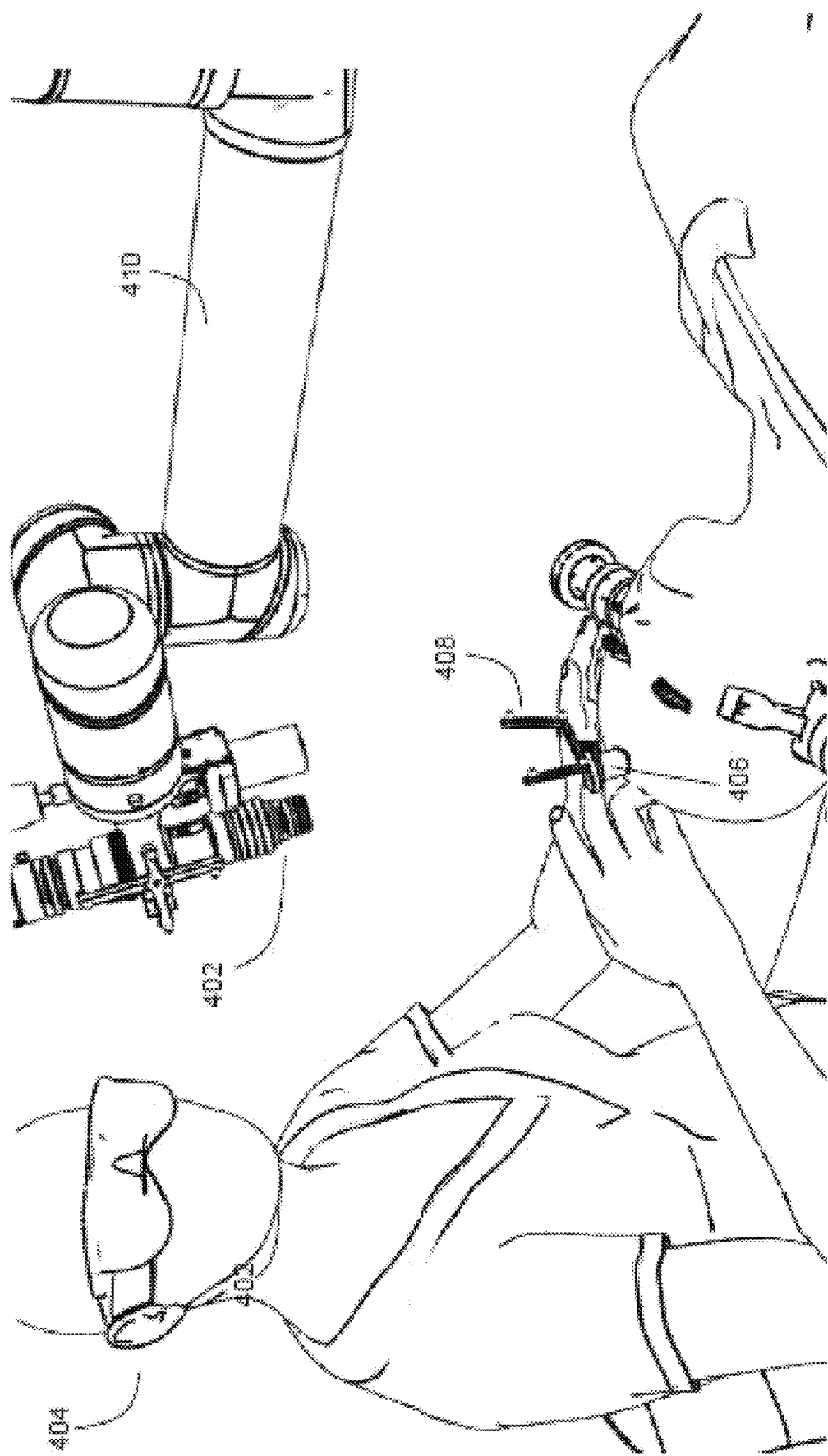
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
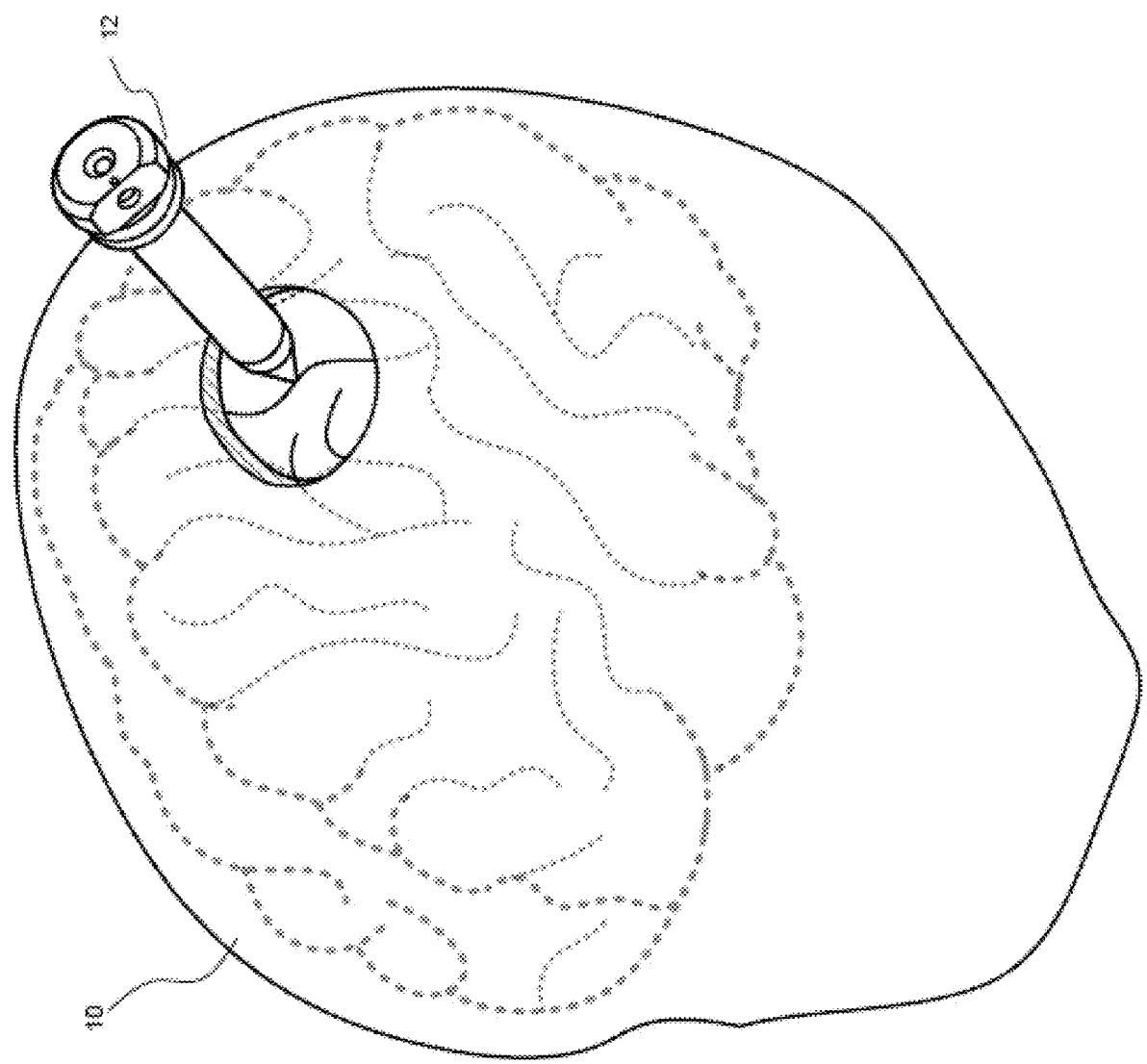
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Figure 6:
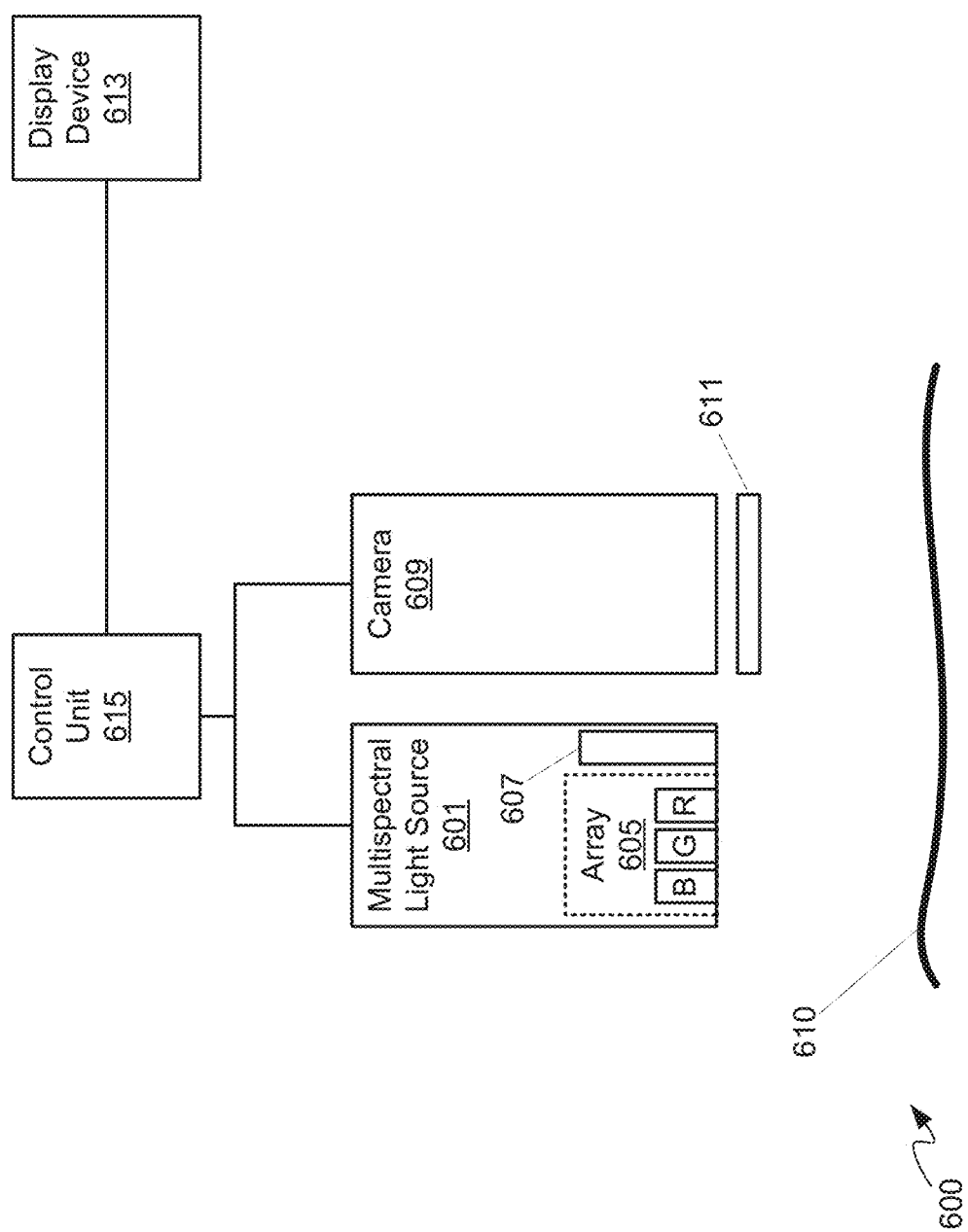
FIG. 6 depicts a multispectral synchronized imaging system, according to non-limiting implementations.

Attention is next directed to FIG. 6, which depicts an example of a multispectral medical imaging system 600 that could be used with access port 12. System 600 comprises: a multispectral light source 601 comprising: a light emitting diode (LED) array 605 comprising: at least one blue LED (as indicated by "B" in FIG. 6), at least one green LED (as indicated by "G" in FIG. 6) and at least one red LED (as indicated by "R" in FIG. 6); and one or more non-visible light sources 607 arranged side by side with LED array 605, each of the at least one blue LED, the at least one green LED, the at least one red LED, and the one or more non-visible light sources 607 being independently addressable such that multispectral light source 601 is configured to emit in a sequence: at least visible white light, and non-visible light in one or more given non-visible frequency ranges; a camera 609 arranged to receive light from a tissue sample 610 illuminated by multispectral light source 601 in the sequence; an optical filter 611 arranged to filter the light from tissue sample 610 received at camera 609, the optical filter configured to: transmit visible light from LED array 605; filter out non-visible light from the one or more non-visible light sources 607 in the one or more given non-visible frequency ranges; and otherwise transmit excited light emitted by tissue sample 610 under excitation by the non-visible light from the one or more non-visible light sources 607; a display device 613; and, at least one control unit 615 configured to: control multispectral light source 601 to emit the sequence; synchronize acquisition of respective images at the camera 609 for each of blue light, green light, the white light, and the excited light received at camera 609, as reflected by tissue sample 610; and, output the respective images in a respective sequence to display device 613.

For clarity, appreciated is that the terms visible and non-visible, as used herein, refer to a human vision system (HVS). Hence, the term "visible light," as used herein, comprises light that is considered visible in a human vision system and/or is visible to an average human being, Similarly, the term "non-visible light," as used herein, comprises light that is considered non-visible in a human vision system and/or is non-visible to an average human being.

While not depicted, multispectral light source 601, camera 609 and optical filter 611 can be adapted for use with access port 12 and/or corridor based surgery and the like. In other words, spectral light source 601, camera 609 and filter 611 can be components of an endoscope, and the like, used with access port 12 and/or corridor based surgery and the like. Put another way, multispectral light source 601, camera 609 and optical filter 611 can be configured for use with a surgical port configured for corridor based surgery, as described in more detail below with respect to FIG. 12.

Components of system 600 will now be described in detail. In particular, multispectral light source 601, which will interchangeably referred to hereafter as light source 601, can comprise an integrated light source, for example, that includes LED array 605 (interchangeably referred to hereafter as array 605) and one or more non-visible light sources 607. While only one LED is depicted for each color LED in array 605 in FIG. 6, array 605 can include arrays of LEDs for each color. One or more non-visible light sources 607 can include, but is not limited, one or more infrared (IR) diodes and/or one or more IR lasers and/or one or more ultraviolet (UV) diodes and/or one or more UV laser.

Camera 609 can include, but is not limited to one or more of a CCD camera, a digital camera, an optical camera, and the like, and is generally configured to acquire digital images.

Optical filter 611, which will be described in more detail below, can comprise a dichroic filter and the like, and can be located at least in front of an image sensor of camera 609 and/or in front of a lens of camera 609. Either way, light imaged by camera 609 is generally filtered by optical filter 611.

As described above, optical filter 611 is configured to: transmit visible light from LED array 605; filter out non-visible light from one or more non-visible light sources 607 in the one or more given non-visible frequency ranges; and otherwise transmit excited light emitted by tissue sample 610 under excitation by the non-visible light from the one or more non-visible light sources 607; a display device 613. In other words, optical filter transmits light from LEDs in array 605, does not transmit light from one or more non-visible light sources 607, but transmits light emitted from tissue sample 610 when excited by non-visible light from one or more non-visible light sources 607.

As such, a transmission spectrum of optical filter 611 is selected for compatibility with one or more non-visible light sources 607, and any specific imaging techniques and/or dyes to be used in tissue sample 610 during surgery. For example, tissue sample 610 can be treated with a given dye, including, but not limited to fluorescence dyes that fluoresce when irradiated by non-visible light (including, but not limited to one or more of PpIX fluorophore, that fluoresces when irradiated by UV light, and ICG fluorophore, that fluoresces when irradiated by IR light). As such, in this example, a transmission spectrum of optical filter 611 can be selected that transmits fluorescent light emitted by tissue sample 610, but does not transmit and/or blocks the excitation light from one or more non-visible light sources 607.

Hence, in some implementations, one or more non-visible light sources 607 comprises an ultraviolet (UV) LED, and the like, and optical filter 611 is configured to filter out UV light from the UV LED, and transmit the excited light emitted by tissue sample 610 under excitation from the UV LED.

Alternatively, in other implementations, one or more non-visible light sources 607 comprises an infrared (IR) laser, and the like, and optical filter 611 is configured to filter out IR light from the IR laser, and transmit the excited light emitted by tissue sample 610 under excitation from the IR laser.

However, in other implementations, one or more non-visible light sources 607 can comprise both a UV light source and an IR light source, and optical filter 611 can be adapted accordingly to block light from both.

Figure 7:
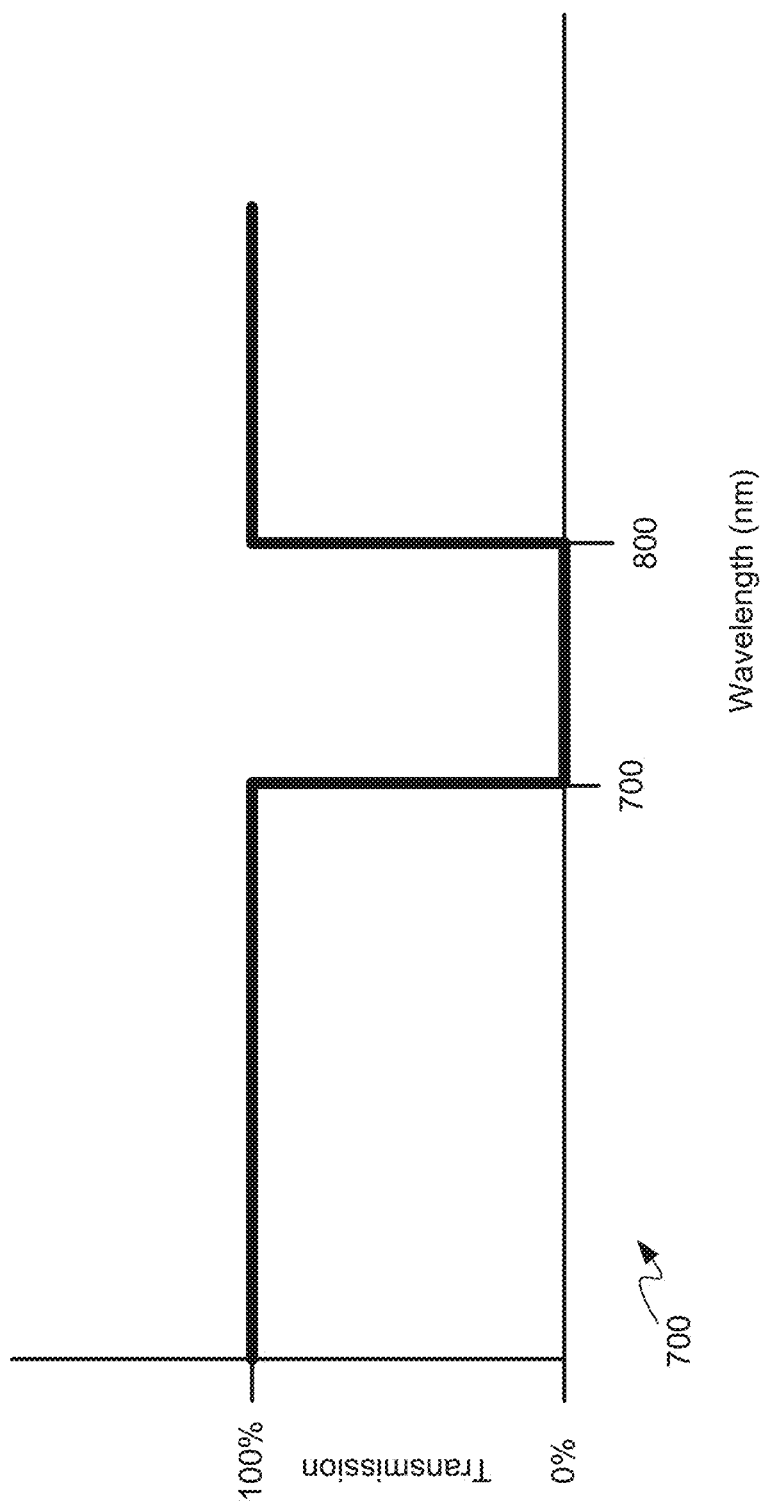
FIG. 7 depicts an example transmission spectrum of an optical filter in the multispectral synchronized imaging system of FIG. 6, according to non-limiting implementations.

Attention is directed to FIG. 7 which depicts a non-limiting transmission spectrum 700 of optical filter 611, assuming that one or more non-visible light sources 607 comprises an infrared (IR) laser, and the like, and optical filter 611 is configured to filter out IR light from the IR laser, and transmit the excited light emitted by tissue sample 610 under excitation from the IR laser. Specifically, it is assumed in FIG. 7 that the IR laser emits light in a range of about 700 nm to about 800 nm and that tissue sample 610 emits light above about 800 nm when irradiated by light from the IR laser. Hence, in the range of about 700 nm to about 800 nm, light is not transmitted by optical filter 611 (e.g. transmission is about 0%), but outside of the range of about 700 nm to about 800 nm, light is transmitted (e.g. transmission is about 100%). Hence, in these implementations, camera 609 can image light in the visible range below 700 nm from LED array 605 that is reflected to camera 609 by tissue sample 610, and camera 609 can also image light emitted by tissue sample 610 when excited by light from one or more non-visible light sources 607.

While a specific range of wavelengths where the light is not transmitted is depicted in FIG. 7, in other implementations, other ranges of wavelengths can be selected that are compatible with light emitted from one or more non-visible light sources 607. Furthermore, while not depicted, optical filter 611 can be further configured to block transmission of light below a visible range of wavelengths and/or in a UV range of wavelengths, and/or configured to block transmission of light above a given wavelength (e.g. above 900 nm, or 1000 nm and/or in the far infrared, to ensure that far IR light does not interfere with operation of system 600)

Returning to FIG. 6, display device 613 can comprise any suitable display device including, but not limited to, cathode ray tubes, flat panel displays, and the like. For example, display device 613 can comprise one or more of monitors 205, 211, as depicted in FIG. 2, and/or displays 305, 311 depicted in FIG. 3.

At least one control unit 615 is generally configured to control light source 601 and display device 613 and to receive images from camera 609. Hence, at least one control unit 615 is interconnected with each of light source 601, camera 609 and display device 613. In some implementations, at least one control unit 615 can comprise control and processing unit 300 depicted in FIG. 3, and/or at least one control unit 615 can be in communication with control and processing unit 300 depicted in FIG. 3 and/or at least one control unit 615 can be under control of communication with control and processing unit 300 depicted in FIG. 3.

At least one control unit 615 can further comprise any suitable combination of computing devices, processors, memory devices and the like. In particular, at least one control unit 615 can comprise one or more of a data acquisition unit, configured to acquire data and/or images at least from camera 609, and an image processing unit, configured to process data and/or images from camera 609 for rendering at display device 613.

In particular, at least one control unit 615 controls control multispectral light source 601 to emit light in a sequence that includes visible white light (e.g. from array 605) and non-visible light (e.g. from one or more non-visible light sources 607). Hence, at least one control unit 615 causes tissue sample 610 to be irradiated with at least white light and non-visible light in a sequence (e.g. see FIG. 8, described below). The sequence can also include blue light emitted from the blue LED, and green light emitted from the green LED.

Tissue sample 610 reflects the white light (and blue light and green light) into camera 609 through optical filter 611, and emits excited light under excitation from the non-visible light from one or more non-visible light sources 607, which is also received at camera 609 through optical filter 611 (which also removes the non-visible light from one or more non-visible light sources 607). Hence, camera 609 alternately (and/or in a sequence), produces optical images of tissue sample 610 when irradiated with white light, blue light and green light, and images of the excited light emitted by tissue sample 610.

Hence at least one control unit 615 is also configured to synchronize acquisition of respective images at camera 609 for each of the blue light, the green light, the white light, and the excited light received at camera 609, as reflected and/or emitted by tissue sample 610. For example, at least one control unit 615 can track when multispectral light source 601 is emitting a particular color and/or type of light (e.g. green, blue, white, non-visible), and can classify an image received from camera 609 simultaneous with such emission as being generated using the particular color and/or type of light. Hence, at least one control unit 615 can coordinate emission of light from multispectral light source 601 with acquisition of images produced by the light at camera 609.

Respective images that result from each particular color and/or type of light is output in a respective sequence to display device 613 for rendering thereupon. Such images can, for example, assist a surgeon with guiding surgical tools in an access port during corridor based surgery. For example, images produced using visible light can be used for an optical view of tissue sample 610, while images produced from excited light from tissue sample 610 can be used for fluorescence guided surgery; indeed, using system 600, a surgeon can switch back and forth between white light guided surgery (and/or surgery using blue light and/or green light) and fluorescence guided surgery.

Indeed, various sequence of light used to irradiate tissue sample 610 are within the scope of present implementations. For example, the sequence can comprise the visible white light, and the non-visible light alternating. Alternatively, the sequence can comprises visible white light, green light, blue light, and the non-visible light, alternating. However, the sequence can also comprise: one or more of a user-configured sequence; and simultaneous emission of light from two or more of the at least one blue LED, the at least one green LED, the at least one red LED. Indeed, any sequence that will assist a surgeon view tissue sample 610 using images rendered at display device 613 is within the scope of present implementations.

In some implementations, at least one control unit 615 can further control intensity of LEDs in array 605. For example, respective relative intensity of each of the at least one blue LED, the at least one green LED, the at least one red LED can be adjusted to change one or more of color temperature of the visible white light and color rendering of respective images output to display device 613. For example, color quality of light and/or white light can be described by two parameters: correlated color temperature (CCT) and color rendering index (CRI), and by respective relative intensity of each of the at least one blue LED, the at least one green LED, the at least one red LED, a given and/or desired CCT and CRI can provided to, in turn, achieve a given color appearance of tissue sample 610, including a CCT and CRI within desired ranges (e.g. for a "good" color appearance).

Figure 8:
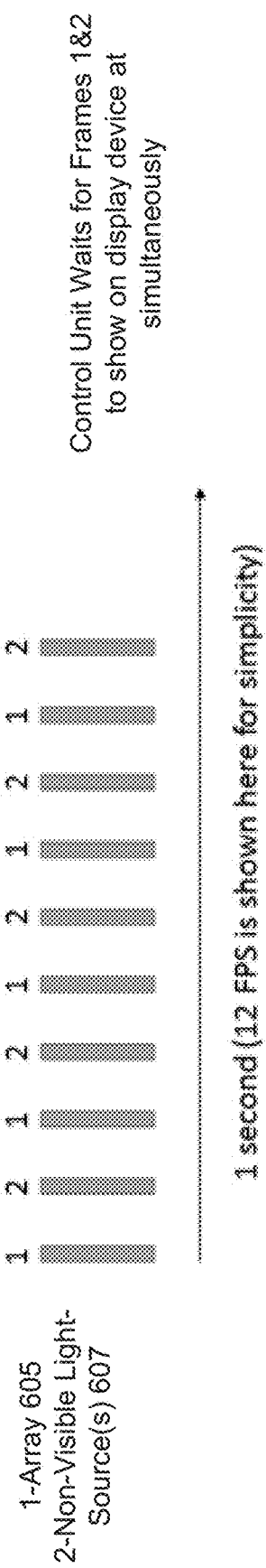
FIG. 8 depicts a light emission sequence of a multispectral light source of the multispectral synchronized imaging system of FIG. 6, according to non-limiting implementations.

In any event, attention is next directed to FIG. 8, which depicts a sample sequence that can be implemented at multispectral light source 601 in which light from array ("1") 605 alternates with non-visible light ("2") from one or more non-visible light sources 607. In particular, the sequence depicted in FIG. 8 comprise the visible white light, and the non-visible light alternating, at a rate of 12 frames per second (FPS), which is also the rate at which the corresponding images are rendered at display device 613.

Indeed, images rendered at display device 613 can be at a rate (with multispectral light source 601 controlled at a corresponding rate) where the images appear to be simultaneously rendered to a human vision system. Hence, for example, images that result from tissue sample 610 being irradiated with white light appear to be combined with images formed from excited light emitted from tissue sample 610, thereby combining white light surgery and fluorescence guided surgery, and the like; in other words, features of tissue sample 610 that are visible only using fluorescence guided surgery are combined at display device 613 with features of tissue sample 610 visible when tissue sample 610 is irradiated with white light.

Hence, at least one control unit 615 can be further configured to output the respective images in the respective sequence to display device 613. In some implementations, such images can be static, for example, one or more acquired images can be rendered at display device 613, statically (e.g. one or more images are acquired and rendered at display device 613 rather than a stream of images). In other implementations, least one control unit 615 can be further configured to output the respective images in the respective sequence to display device 613 in a video stream and/or at a rate where the respective images appear simultaneously rendered to a human vision system. For example, in some implementations, such rates can, include, but are not limited to, 12 FPS and higher. However, the rate of rendering images at display device 613 can also depend on a rate at which images are acquired at camera 609; for example, if camera acquires images at a rate of 60 Hz, an output rate of images at display device 613 can be about half the camera rate and/or about 30 Hz, assuming that two frames are captured, one visible and one-non-visible (e.g. see FIG. 8, described below). However, other rates are within the scope of present implementations and can depend both on a configuration of camera 609 and/or a configuration of display device 613 and/or a number of light sources in multispectral light source 601 and/or a number of frames dedicated to each of the light sources in multispectral light source 601.

Indeed, LEDs of array 605, as well as one or more non-visible light sources 607 can be selected based on what rate images are to be provided at display device 613. For example, specific LEDs types (for array 605) and laser diodes (for one or more non-visible light sources 607) can be selected where transient times are less than a microsecond.

Similarly, wavelengths of each of LEDs of array 605 and laser diodes for one or more non-visible light sources 607 can be selected which maximize a number of modalities that can be measured in conjunction with the camera synchronization. In a particular non-limiting implementation, two types of laser diodes can be used at one or more non-visible light sources 607 that emit both UV light and IR light; in one particular non-limiting implementation, array 605 can comprise: one or more 460 nm Blue LEDs, one or more 530 nm Green LEDs; and one or more 620 nm Red LEDs, and non-visible light sources 607 can comprise: one or more 415 nm UV LEDs, and one or more 785 nm IR laser diodes. As such, a transmission spectrum of optical filter 611 is adapted to transmit light in the range if the LEDs of array 605, and to block light emitted by both the one or more 415 nm UV LEDs, and the one or more 785 nm IR laser diodes.

Use of such LEDs, UV LEDs and IR laser diodes can enable several modes and/or use cases in system 600 which can include, but is not limited to:
   UV LED: excitation of PpIX fluorophore for better tumor margin delineation (e.g. to produce excited light from a tissue sample);
   Blue/Green/Red LEDs: trichromatic white light with tunable CRI (color rendering index);
   Blue/Green interleaved: quantitative measure of blood oxygenation and volume (i.e. the sequence can include blue and green light);
   Diffused IR laser: excitation of ICG fluorophore for angiography (e.g. to produce excited light from a tissue sample); and,
   Speckled IR laser: quantitative measure of the blood flow.
In the last use case, system 600 can be modified to include at least a second optical filter that can be exchanged for optical filter 611, the second optical filter and optical filer 611 being exchangeable, depending on the operating mode.

Figure 9:
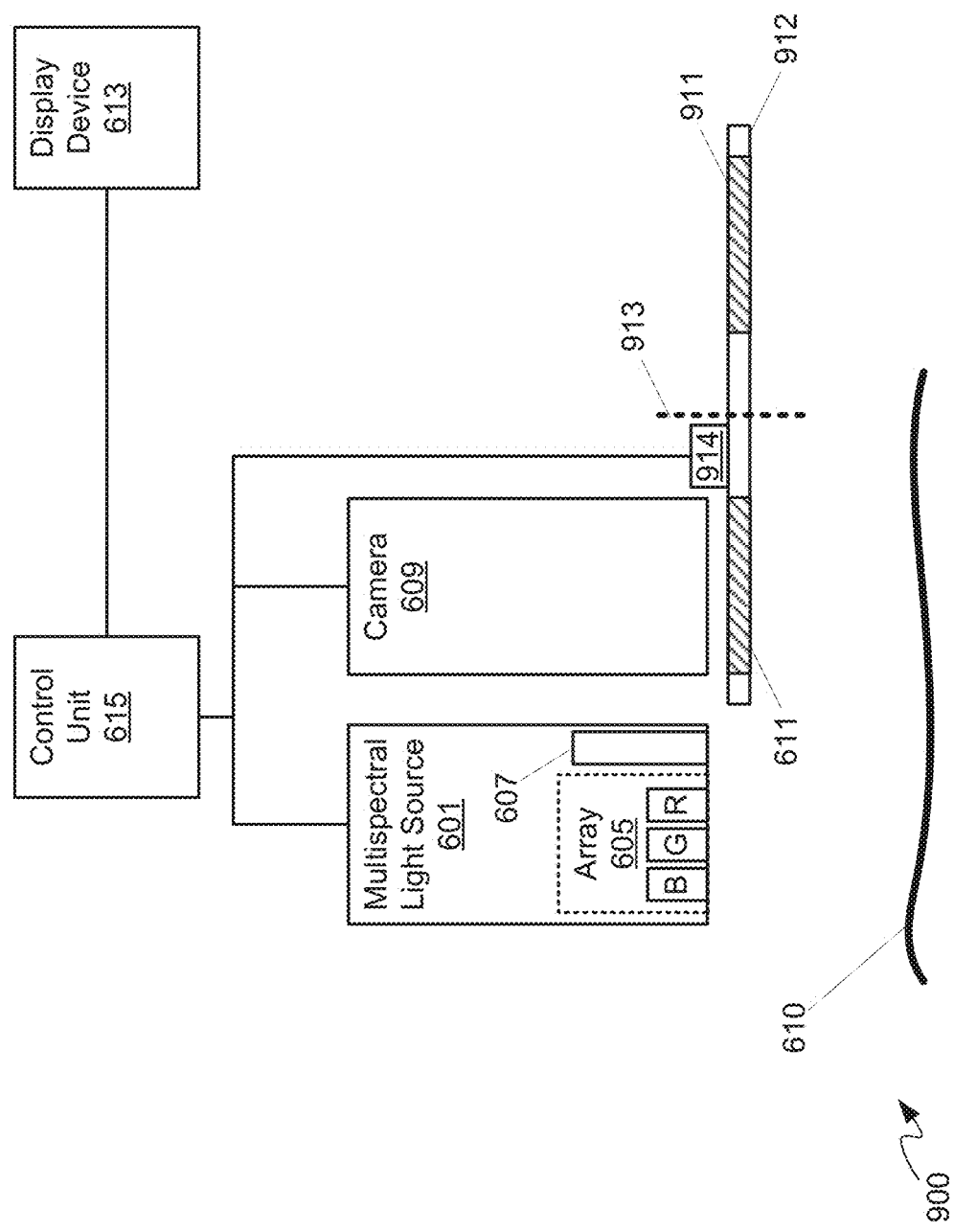
FIG. 9 depicts a multispectral synchronized imaging system adapted for use with multiple optical filters, according to non-limiting implementations.

For example, attention is next directed to FIG. 9 which depicts system 900 and is substantially similar to system 600, with like elements having like numbers, however in system 900, one or more non-visible light sources 607 specifically comprises an infrared (IR) laser, and system 900 further comprising a second optical filter 911, that can be exchanged for optical filter 611 under control by at least one control unit 615, second optical filter 911 configured to transmit light from the IR laser.

For example, as depicted, optical filters 611, 911 can be mounted in a filter wheel 912 configured to rotate about an axis 913. In other words, in FIG. 9 depicts a cross-sectional view of filter wheel 912. Furthermore, filter wheel 912 further comprises apparatus 914 configure to control a position of optical filters 611, 911 with respect to camera 609, apparatus 914 in communication with at least one control unit 615. For example, apparatus 914 can comprise a stepper motor, and the like. Alternatively optical filters 611, 911 can be mounted to a slideable arm, and the like, configured to exchange optical filters 611, 911 under control by at least one control unit 615; indeed, any device for exchanging optical filters 611, 911 under control by at least one control unit 615 is within the scope of present implementations, assuming such devices are compatible with the surgical techniques to be used with system 900.

Figure 10:
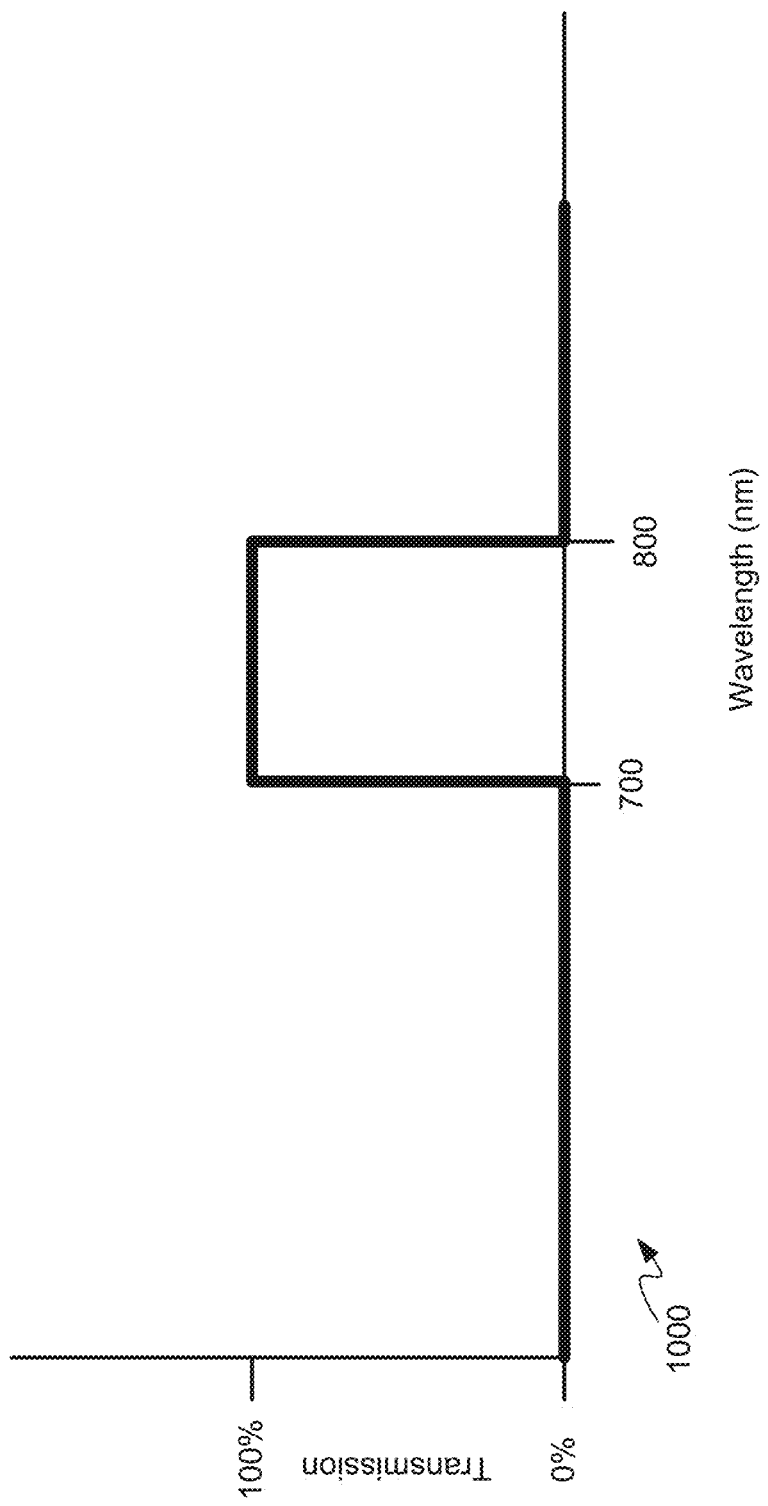
FIG. 10 depicts an example transmission spectrum of one of the optical filters in the multispectral synchronized imaging system of FIG. 9, according to non-limiting implementations.

Attention is next directed to FIG. 10, which depicts a transmission spectrum 1000 of optical filter 911. In contrast to the transmission spectrum 700 of optical filter 611 depicted in FIG. 7, transmission spectrum 1000 of optical filter 911 transmits light from IR laser of one or more non-visible light sources 607 in a range of about 700 nm to about 800 nm, and does not transmit light outside this range.

Hence, optical filter 611 can be used to operate system 900 in a manner similar to system 600 and described above. However, optical filter 911 can be exchanged for optical filter 611, and the IR laser of one or more non-visible light sources 607 can be operated in a speckled mode which can be used to quantitatively measure blood flow in tissue sample 610.

Hence, system 900 and/or IR laser of one or more non-visible light sources 607, can be operated in at least two modes. In particular, the IR laser can be operated in one of a diffused mode, when optical filter 611 is filtering light to camera 609, and a speckled mode when second optical filter 911 is filtering light to camera 609. In other words, the diffuse mode can be used when operating system 900 in a manner similar to system 600.

In yet further implementations, system 900 can be used in a third mode. In particular, the IR laser can be operated in a speckled mode when second optical filter 911 is filtering light to camera 609, and the sequence of light emitted by multispectral light source 601 includes green light emitted from the green LED, and blue light emitted from the blue LED, when optical filter 611 is filtering light to camera 609, speckled laser light from the IR laser in the speckled mode, the green light and the blue light used for functional imaging of blood flow in the tissue sample. In other words in the third mode, when optical filter 611 is filtering light to camera 609, green light and blue light can be used in sequence to irradiate tissue sample 610, and then optical filters 611, 911 can be exchanged, and the IR laser can be operated in a speckled mode (though the specific sequence of colors irradiating tissue sample 610 is generally irrelevant, presuming at least one control unit 615 is synchronizing such irradiation with filter position, and image acquisition).

In yet further implementations, one or more of systems 600, 900 can be adapted to include further optical filters and further light sources. For example, in some implementations, filter wheel 912 can be adapted to include three optical filters having the following transmission characteristics:

Filter 1: Transmits light in a visible range of about 400 nm to about 700 nm, allowing visible light reflected from tissue sample 610 to be imaged by camera 609, and which can be used for "standard" white light surgery.

Filter 2: Transmits light in an extended range of about 400 nm to about 800 nm, allowing light from an IR laser operated in a speckled mode to be imaged by camera 609, and which can be used for concurrent white light surgery and quantitative blood physiology measurement.

Filter 3: Transmits light in a fluorescent range of about 430 nm to about 700 nm, and from about 820 nm to about 860 nm, which blocks light from both UV and IR light sources while allowing light from the emission of PpIX & ICG from tissue sample 610 to be imaged by camera 609.

In other words, optical filters respective to light emitted from multispectral light source 601 can be used depending on a mode of operation of the system and what wavelengths of light are being reflected and/or emitted by tissue sample 610.

Figure 11:
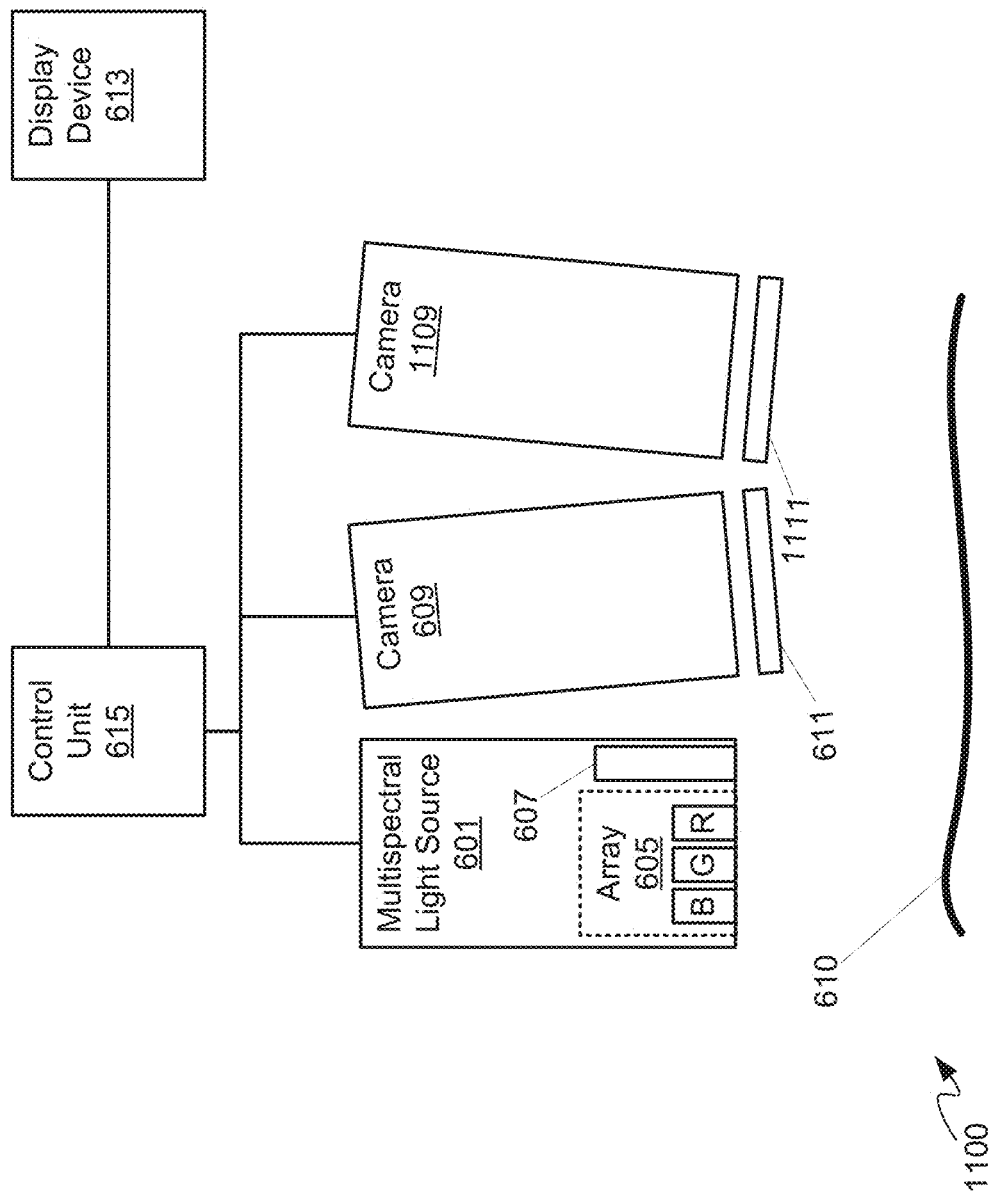
FIG. 11 depicts a multispectral synchronized imaging system adapted for use with two cameras, according to non-limiting implementations.

Persons skilled in the art will appreciate that there are yet more alternative implementations and modifications possible. For example, attention is next directed to FIG. 11 which depicts a system 1100 that is substantially similar to system 600, with like elements having like numbers. However, system 1100 further comprises: a second camera 1109 arranged relative to camera 609 to acquire three-dimensional images of tissue sample 610; hence, as depicted cameras 609, 1109 can be angled and/or positioned to image a same region of tissue sample 610. System 1100 further comprises a second optical filter 1111, positioned to filter light into second camera 1109, second optical filter 1111 configured to: transmit visible light from the LED array 605 and transmit non-visible light from one or more non-visible light sources 607 in the one or more given non-visible frequency ranges. For example, second optical filter 1111 can be configured to transmits light in a fluorescent range of about 430 nm to about 700 nm, and from about 820 nm to about 860 nm, which blocks light from both UV and IR light sources while allowing light from the emission of PpIX & ICG from tissue sample 610 to be imaged by camera 1109; such implementations assume that the one or more non-visible light sources 607 comprises an IR laser, which can be operable in one of a diffused mode and a speckled mode, and a UV laser.

Hence, using two sets of cameras and respective optical filters, different modes of imaging tissue sample 610 can be performed simultaneously. Alternatively, camera 609 and second camera 1109 can be configured to capture images independent of one another, such that system 1100 can be operated in different modes at different times.

Persons skilled in the art will appreciate that there are yet more alternative implementations and modifications possible. For example, in some implementations, one or more of system 600, 900, 1100 can further comprise a thermal camera arranged to receive light from tissue sample 610 illuminated by the multispectral light source 601 in the sequence, thereby performing thermal imaging of tissue sample 610; for example, in system 100, camera 1109 can comprise a thermal imaging camera and optical filter 1111 can either be removed from system 1100 or adapted to transmit light in a thermal imaging range.

Furthermore, in some implementations, light sources, filters and cameras can be packaged together in an apparatus compatible for use with an access port, such as access port 12. For example, attention is directed to FIG. 12, which depicts system 600, in which multispectral light source 601, camera 609, and optical filter 611 are assumed to be packaged in an apparatus 1250, which can comprise an endoscope and the like; as depicted, apparatus 1250 has been inserted through access port 12, depicted in cross-section.

As depicted, apparatus 1250 comprises an optional tracking device 1255 attached to a proximal end apparatus 1250. In other words, as depicted, system 600 optionally comprises tracking device 1255 configured to be tracked by a navigation system. Tracking device 1255 is generally configured to be tracked by a navigation system external to system 600, for example a navigation system that is part of surgical system, such as that depicted in FIGS. 1 to 4. While not depicted apparatus 1250 can further comprise a mount configured to removably attach tracking device 1255 at a proximal end thereof (e.g. an end that is away from tissue being imaged). Tracking device 1255 is generally positioned so that a camera, and the like, of a surgical navigation system may track a position of tracking device 1255 and hence a relative position of a distal end of apparatus 1250 (e.g. an end of apparatus 1250 closest to tissue sample 610). As depicted, tracking device 1255 comprises four reflective spheres arranged in a configuration where each sphere is located at about a corner of a square. However, other numbers of spheres and other configurations are within the scope of present implementations. In particular or more of a number, arrangement, and configuration of such spheres may be selected to provide a given tracking accuracy, including, but not limited to, a tracking accuracy that is less than about half a diameter of a sensing array surface. However, tracking device 1255 may include tracking devices other than reflective spheres. For example, in some implementations, tracking device 1255 may include a flexible sheath configured to measure tip position deflection, for example deflection of a tip of the flexible sheath. Furthermore, system 600 can be adapted to include one or more tracking devices.

Furthermore, at least one control unit 615 can comprises one or more ports configured for communicate with one or more of: surgical navigation system; external computing devices; electronic surgical devices; trackers; and infrared trackers.

Persons skilled in the art will appreciate that there are yet more alternative implementations and modifications possible. For example, at least one control unit 615 can be configured to implement various image processing algorithms including, but not limited to: amplification of the color dynamics around the edge of the tumor margin under FGS mode, image fusion between WLS and FGS modes, division of the light reflectance under blue light to that of green light for blood oxygenation and volume computations, spatial computation under speckled laser illumination for blood perfusion.

When using two cameras, which can be used for combined three-dimensional vision, as in system 1100, image processing algorithms implemented by at least one control unit 615 can further include finding parameters to warp image from each camera onto another. In some of these implementations, at least one control unit 615 can control multispectral light source 601 to intermittently flash blue light from the blue LED into one camera and flash blue light from the blue LED into the other camera (e.g, assuming that at least one control unit 615 is synchronizing images from the cameras) to obtain a quantitative blood physiology while warping and merging images from each camera into a single image.

Figure 12:
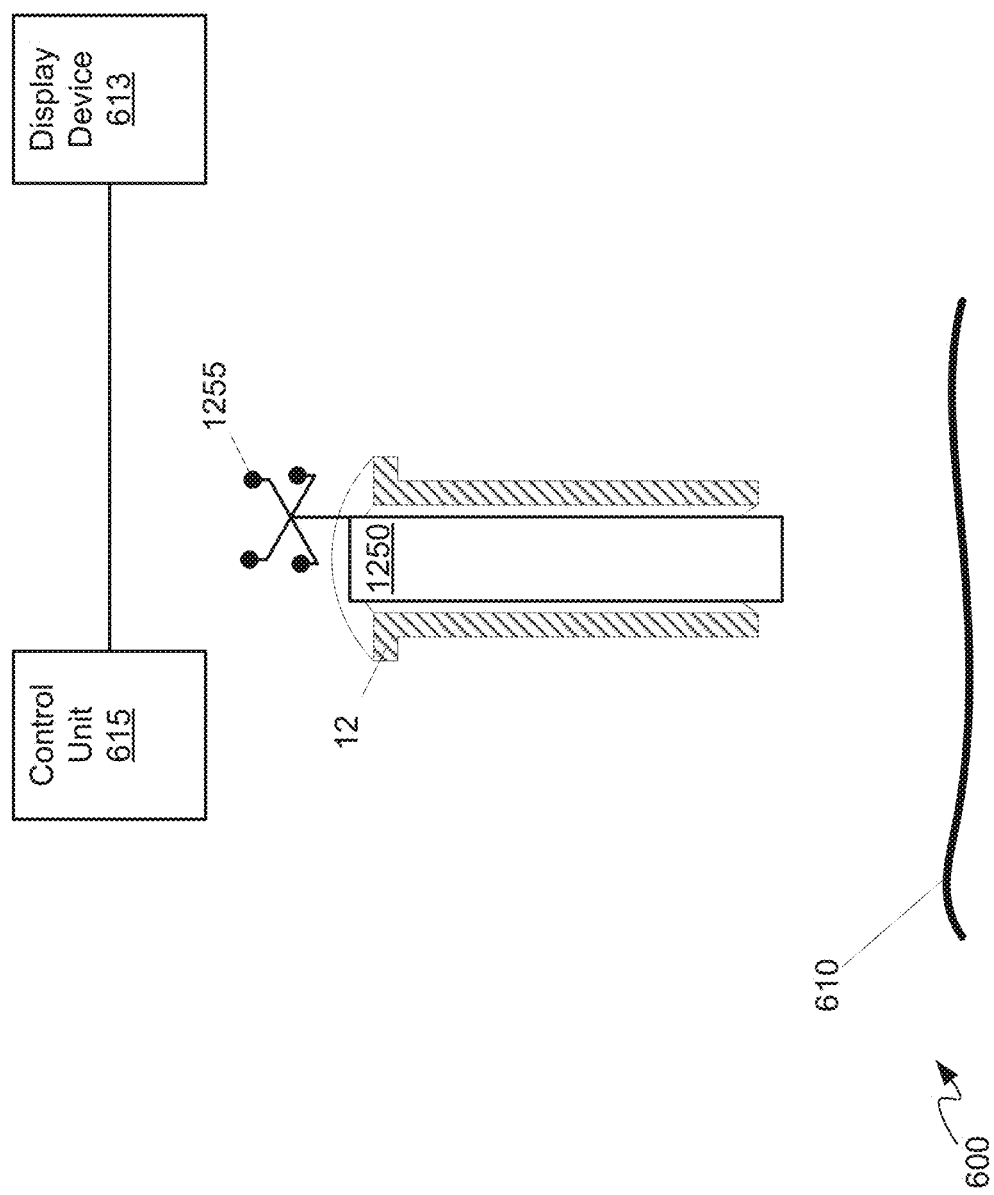
FIG. 12 depicts a multispectral synchronized imaging system adapted for use with an access port for corridor based surgery, according to non-limiting implementations.

In yet further implementations, systems described herein can be adapted to include external sources and at least one control unit 615 can either comprise or be a component of other surgical systems and/or be in communication with a main control hub of surgical system. In such implementations, at given intervals (e.g. every second), such a main control hub cause camera acquisition of systems described herein to stop such that external source can be used to perform other imaging techniques, including, but not limited to, intraoperative Raman spectroscopy. Furthermore, when tracking devices are used with systems described herein (e.g. as depicted in FIG. 12), and such tracking devices are tracked using light in an infrared spectrum such infrared light can introduce artefacts from pulsing infrared diodes on the acquired images unless optical filters described herein are further adapted to filter out such artefacts. For example, the sequence depicted in FIG. 8 could be modified to include an infrared tracking pulse in the 700 nm to 800 nm region between frames and/or within a frame that illuminates apparatus 1255, which is detected by a tracking system, but images of apparatus 1255 and/or the tracking pulse, is filtered out of camera 609 using optical filter 611 (e.g. see FIG. 7). Hence, by using system 600, infrared tracking can be used in conjunction with FGS without introducing artefacts into images of tissue sample 610 rendered at display device 613 from camera 609.

In yet further implementations, at least one control device 615 can be adapted to perform sub-frame synchronization, for example by controlling camera shutter speeds and/or camera "sync" pulses to stagger image acquisition on a sub-frame basis; such a feature can obviate reductions in frame rate in a global acquisition of images, for example in different spectral and/or wavelength ranges. Such a feature can also be referred to as "time multiplexing of image acquisition and illumination", which can be used for different modalities of systems 600, 900, 1100 that include a plurality of cameras that can acquire images in different spectral and/or wavelength ranges. For example, systems 600, 900, 1100 can be used as a kind of "global image and illumination scheduler" using the mentioned sync pulses, and the like, which can ensure that the various image acquisitions in the different spectral and/or wavelength ranges (e.g. tracking, visible, non-visible, etc.) don't interfere with each other as they all require different lighting and capture environments. For example, in a specific non-limiting example, such sub-frame synchronization could be implemented in a system comprising multiple cameras, each with a frame rate of 60 Hz; hence a fame is acquired every $\frac{1}{60}$ of a second (however, camera speeds are often faster, and such acquisitions can occur at rates on the order of every $\frac{1}{250}$ of a second to every $\frac{1}{1000}$ of a second, and faster); in such implementations, image capture times of each camera can be slightly off-set with respect to one another, and images from each camera can be acquired within the $\frac{1}{60}$th of a second, within different spectral and/or wavelength ranges, and hence multispectral image can be acquired without reducing frame rate.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A multispectral synchronized imaging system, comprising:
a multispectral light source configured to illuminate tissue, the multispectral light source comprising:
a light emitting diode (LED) array configured to emit visible light including visible white light, the LED array comprising:
at least one blue LED configured to emit blue light,
at least one green LED configured to emit green light, and
at least one red LED configured to emit red light,
wherein each of the at least one blue LED, the at least one green LED, the at least one red LED is individually addressable; and
one or more non-visible light sources configured to emit non-visible light in one or more given non-visible frequency ranges, wherein the one or more non-visible light sources:
are arranged side by side with the LED array,
are independently addressable, and
comprise an infrared (IR) laser, wherein the one or more given non-visible frequency ranges comprise an IR frequency range, and the non-visible light comprises IR light emitted from the IR laser,
a first camera arranged to capture images of the tissue by receiving light reflected from or emitted by the tissue;
a first optical filter and a second optical filter;
a filter positioning device configured to selectively position a selected one of the first optical filter and the second optical filter relative to the first camera such that the selected optical filter positioned relative to the first camera filters said light reflected from or emitted by the tissue prior to being received by the first camera,
wherein, when the first optical filter, as the selected optical filter, is positioned by the filter positioning device relative to the first camera and the visible white light from the LED array illuminating the tissue reflects off the tissue, the first optical filter is configured to: transmit the reflected visible white light to the first camera;
wherein, when the first optical filter, as the selected optical filter, is positioned by the filter positioning device relative to the first camera and the non-visible light from the one or more non-visible light sources in the one or more given non-visible frequency ranges illuminating the tissue reflects off the tissue and excites the tissue to emit a first tissue-emitted light, the first optical filter is configured to: filter the reflected non-visible light so as to be blocked from being received by the first camera, and transmit the first tissue-emitted light to the first camera;
wherein, when the first optical filter, as the selected optical filter, is positioned by the filter positioning device relative to the first camera and the IR light from the IR laser illuminating the tissue reflects off the tissue and excites the tissue to emit a second tissue-emitted light, the first optical filter is configured to: filter the reflected IR light so as to be blocked from being received by the first camera, and transmit the second tissue-emitted light to the first camera; and
wherein, when the second optical filter, as the selected optical filter, is positioned by the filter positioning device relative to the first camera and the IR light from the IR laser illuminating the tissue reflects off the tissue, the second optical filter configured to:
transmit the reflected IR light to the first camera;
a display device;
at least one control unit configured to:
control the multispectral light source to emit, in a sequence, at least:
the visible white light,
the non-visible light, and
simultaneously at least two or more selected from the group consisting of the blue light, the green light, and the red light,
wherein the sequence comprises one or more user configured sequence(s);
control the multispectral light source, the filter positioning device, and the camera in a synchronized and alternating manner to acquire first images and second images in an alternating manner wherein:
the first images are captured by the first camera for each illumination of the tissue by multispectral light source with the blue light, the green light, the visible white light, the IR light, and the non-visible light, while the first optical filter, as the selected optical filter, is positioned by filter positioning device relative to the first camera; and
second images are acquired for illumination of the tissue by the multispectral light source with the IR light, while the second optical filter, as the selected optical filter, is positioned by the filter positioning device relative to the first camera; and
respectively output the first images and the second images to the display device; and
wherein the at least one control unit is further configured to:
enable the multispectral light source to operate in a first mode, whereby diffused IR light is emitted;
control the filter positioning device to position the first optical filter, as the selected optical filter, relative to the first camera so as to filter the diffused IR light from the first camera while acquiring the first images, whereby the first images from the first camera comprise fluorescence imaging images;
output the fluorescence imaging images to the display device;
enable the multispectral light source to operate in a second mode, whereby coherent IR light is emitted;
control the filter positioning device to position the second optical filter, as the selected optical filter, relative to the first camera so as to transmit the coherent IR light to the first camera while acquiring the second images, whereby the second images comprise functional imaging of blood flow in the tissue;
process the first images and the second images to quantitatively measure blood flow in the tissue sample; and
output the first images and the second images to the display device along with quantitative measurements of the blood flow.

2. The multispectral synchronized imaging system of claim 1, wherein the one or more non-visible light sources further comprises an ultraviolet (UV) light source, and
wherein the first optical filter is further configured to:
transmit light in a range of 430 nm to 700 nm, and from 820 nm to 860 nm to allow light from fluorescent emission of one or more of PpIX (Protoporphyrin IX) and ICG (Indocyanine green) administered to the tissue to be imaged by the first camera; and
block both UV light emitted from the UV light source and reflected off the tissue and the IR light emitted from the IR laser and reflected off the tissue from entering the first camera.

3. The multispectral synchronized imaging system of claim 1, wherein the at least one control unit is further configured to:
control the filter positioning device to position the first optical filter, as the selected optical filter, relative to the first camera so as to filter out the reflected IR light from being received by the first camera;
control the at least one green LED and the at least one blue LED to emit, in the sequence, the green light and the blue light respectively to illuminate the tissue;
control the first camera to acquire the first images of the tissue under illumination by the green light and the blue light; and
process the first images to determine tissue oxygenation of the tissue sample.

4. The multispectral synchronized imaging system of claim 1, wherein the sequence comprises emitting the visible white light, and the non-visible light in an alternating manner.

5. The multispectral synchronized imaging system of claim 1, wherein the sequence further comprises emitting the visible white light, the green light, the blue light, and the non-visible light in an alternating manner.

6. The multispectral synchronized imaging system of claim 1, wherein the at least one control unit is configured to control the multispectral light source to adjust a respective relative intensity of each of the at least one blue LED, the at least one green LED, the at least one red LED to change one or more of:
a color temperature of the visible white light; and
a color rendering of the first images and the second images output to the display device.

7. The multispectral synchronized imaging system of claim 1, further comprising: a second camera arranged relative to the first camera to acquire three-dimensional images of the tissue,
wherein the at least one control unit is further configured to determine parameters to warp together images captured by the first camera with images captured by the second camera.

8. The multispectral synchronized imaging system of claim 7, wherein the first camera and the second camera are configured to capture images independent of one another such that one of the first camera and the second camera captures images at times when the other of the first camera and the second camera does not capture images and vice versa.

9. The multispectral synchronized imaging system of claim 7, wherein the at least one control unit is further configured to control the first camera and the second camera such that image capture times of each of the first camera and the second camera are off-set with respect to one another such that images captured by each of the first camera and the second camera are captured within 1/60th of a second of each other.

10. The multispectral synchronized imaging system of claim 1, wherein the at least one control unit is further configured to output the first images and the second images to the display device at a rate of 12 frames per second or higher.

11. The multispectral synchronized imaging system of claim 1, wherein the first camera comprises an optical camera.

12. The multispectral synchronized imaging system of claim 1, further comprising a thermal camera arranged to capture images by receiving the light reflected from of emitted by the tissue.

13. The multispectral synchronized imaging system of claim 12, further comprising a third optical filter disposed in relation to the thermal camera, wherein the third optical filter is configured to transmit light in a thermal imaging frequency range.

14. The multispectral synchronized imaging system of claim 1, wherein the at least one control unit comprises one or more ports, wherein the at least one control unit is configured to communicate, via the or more ports, with one or more of: external computing devices; electronic surgical devices; trackers; and infrared trackers.

15. The multispectral synchronized imaging system of claim 1, wherein the multispectral light source, the first camera, the first optical filter, the second optical filter, and the filter positioning device are packaged together for insertion through a surgical port for corridor based surgery.

16. The multispectral synchronized imaging system of claim 1, further comprising a second camera disposed and configured, in relation to the first camera, in a manner enabling one of simultaneously imaging a same region of the tissue and asynchronously imaging the same region of the tissue,
wherein the second camera is further configured to acquire three-dimensional images of the tissue,
wherein the first optical filter is disposed in relation to the first camera and the second optical filter disposed in relation the second camera, and
wherein the second optical filter further configured to:
transmit the visible light from the LED array reflected off the tissue; and
transmit the non-visible light from the one or more non-visible light sources in the one or more given non-visible frequency ranges reflected off the tissue,
wherein the first camera with the first optical filer and the second camera with the second optical filter respectively enable said one of simultaneously imaging the same region of the tissue sample and asynchronously imaging the same region of the tissue sample in distinct imaging modes.

17. The multispectral synchronized imaging system of claim 16, wherein the multispectral light source, the first filter, the second filter, the filter positioning device, the first camera, and the second camera are packaged together in or to form an endoscope compatible for use with an access port.

18. The multispectral synchronized imaging system of claim 17, further comprising at least one tracking device removably coupled with a proximal end of the endoscope, the at least one tracking device configured to be tracked by an external navigation system via infrared tracking, and wherein at least one of the first optical filter and the second optical filter is further configured to filter an artefact caused by the infrared tracking.

19. The multispectral synchronized imaging system of claim 18, wherein the at least one control unit is further configured to control illumination by the multispectral light source and capturing of images by the first camera and the second camera for sub-frame synchronization by controlling at least one of a camera shutter speed and a camera synchronization pulse to stagger image acquisition of the first camera and the second camera on a sub-frame basis, so as to effect time multiplexing of the image acquisition and the illumination.

20. The multispectral synchronized imaging system of claim 1, further comprising a second camera arranged relative to the first camera, wherein the at least one control unit is further configured to perform at least one of:
communicate with at least one of:
a surgical navigation system,
an external computing device,
an electronic surgical device,
at least one tracker, and
at least one infrared tracker;
implement at least one image processing algorithm comprising at least one of:
an amplification algorithm for amplifying color dynamics around an edge of a tumor margin under a fluorescence guided surgery (FGS) mode,
an image fusion algorithm for fusing imaging between a white light surgery (WLS) mode and the FGS mode,
a division algorithm for dividing light reflectance under the blue light from light reflectance under the green light for blood oxygenation computation and volume computation,
a spatial computation algorithm for computing speckled laser illumination for blood perfusion, and
an algorithm for finding parameters to warp an image captured by the first camera onto an image captured by the second camera;
control the multispectral light source to intermittently flash the blue light from the blue LED and reflected by the tissue into the first camera to capture a first blue light image and flash the blue light from the blue LED and reflected by the tissue into the second camera to capture a second blue light image to obtain a quantitative blood physiology while warping and merging the first blue light image and the second blue light image into a single image; and
communicate with a main control hub of a surgical system, wherein the main control hub is configured to cause an external light source to perform intraoperative Raman spectroscopy.

* * * * *